(12) United States Patent
Mirza et al.

(10) Patent No.: US 9,931,133 B2
(45) Date of Patent: Apr. 3, 2018

(54) COMPACT ENDOSCOPIC SURGICAL DEVICE AND METHOD OF USE THEREOF

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 201 days.

(21) Appl. No.: 15/080,116

(22) Filed: Mar. 24, 2016

(65) Prior Publication Data
US 2017/0273706 A1 Sep. 28, 2017

(51) Int. Cl.
| | |
|---|---|
| A61B 17/32 | (2006.01) |
| A61B 17/22 | (2006.01) |
| A61B 17/3211 | (2006.01) |
| A61B 17/3205 | (2006.01) |
| A61B 17/00 | (2006.01) |

(52) U.S. Cl.
CPC ...... *A61B 17/320016* (2013.01); *A61B 17/22* (2013.01); *A61B 17/3205* (2013.01); *A61B 17/3211* (2013.01); *A61B 2017/00371* (2013.01)

(58) Field of Classification Search
CPC . A61B 17/3205; A61B 17/22; A61B 17/3211; A61B 2017/00371; E05C 19/008; E05C 19/022
See application file for complete search history.

(56) References Cited

U.S. PATENT DOCUMENTS

| | | | |
|---|---|---|---|
| 5,931,849 A | 8/1999 | Desvignes et al. | |
| 6,706,050 B1 | 3/2004 | Giannadakis et al. | |
| 2005/0250984 A1 | 11/2005 | Lam et al. | |
| 2006/0276811 A1* | 12/2006 | Copa ...................... | A61B 17/11 606/153 |
| 2014/0066709 A1* | 3/2014 | Mirza .............. | A61B 17/32002 600/106 |

OTHER PUBLICATIONS

International Search Report and Written Opinion of the International Searching Authority, Application No. PCT/US2016/024250, dated Jun. 24, 2016.

* cited by examiner

*Primary Examiner* — Richard Louis
(74) *Attorney, Agent, or Firm* — Ping Wang; Andrews Kurth Kenyon LLP (57) ABSTRACT

A uniportal surgical device having a slotted clear cannula, a blade and a housing, wherein the cannula is attached to the housing, and wherein the blade is enclosed in the housing and is slidable into the cannula is disclosed. The device further has a device for locking a viewing device in place relative to other components of the device. A method for a performing an operative procedure on a target tissue in a subject using the uniportal surgical device is also described.

20 Claims, 3 Drawing Sheets

COMPACT ENDOSCOPIC SURGICAL DEVICE AND METHOD OF USE THEREOF

FIELD

This application generally relates to medical devices. In particular, the application relates to devices and methods for uniportal endoscopic or arthroscopic surgery, e.g., for fascia, tendon or ligament release surgery.

BACKGROUND

Endoscopic and arthroscopic surgery are minimally invasive surgical procedures that are performed through small incisions or natural body openings. These procedures typically involve use of specialized devices and remote-control manipulation of instruments with indirect observation of the surgical field through an arthroscope, endoscope or similar device. Comparing to open surgery, endoscopic and arthroscopic surgery may result in shorter hospital stays, or allow outpatient treatment.

The Plantar fascia is a thick band of connective tissue running along the bottom (plantar) surface of the foot, connecting the heel bone to the toes. It helps support the overall shape of the foot, especially when standing. Irritation or scarring of the plantar fascia, known as plantar fasciitis, is one of the most common causes of heel pain or pain in the plantar surface of the foot.

Typical first line treatments for plantar fasciitis are non-surgical interventions. Such treatments include therapeutic exercises to stretch the plantar fascia, orthotic inserts such as arch supports, non-steroidal anti-inflammatory drugs (NSAIDs) and steroid injections. Failure of these remedies to relieve the condition may lead to a need for surgical plantar fascia release.

Conventional surgical techniques and equipment for plantar fascia release require a fairly large incision on the foot above the heel pad, where the thicker skin of the sole meets the thinner skin of the back of the heel, or an incision is made on the bottom of the foot. These techniques can require a longer period of recovery than endoscopic methods and have greater levels of post-operative pain due to the incision size and level of manipulation during the procedure. Following conventional open surgery techniques, a patient may need to wear a non-weight-bearing cast or brace for 2 to 3 weeks after surgery to allow tissues to heal.

Typically, endoscopic surgery has involved a number of steps and separate devices for performing plantar fascia division. Incisions are made on both sides of the heel and a path passing across the plantar fascia is opened between the two incisions using a blunt instrument so that a cannula can be inserted into the path. In order to smoothly insert the cannula, the central lumen of the cannula must be filled with a device, such as an obturator. The obturator is then removed and a viewing device, such as an endoscope or arthroscope, is inserted into the cannula from one side to view the plantar fascia. A knife is then advanced into the cannula from the other side and the knife and viewing device must them be moved together for viewing and dividing the plantar fascia. This requires the practitioner to move both hands in concert on opposite side of the foot. This technique allows the patient limited weight-bearing immediately after the procedure and less pain than the conventional open surgery, but still requires multiple incisions and the introduction of multiple surgical tools through those incisions.

Accordingly, the ability to perform endoscopic or arthroscopic surgeries in the lower extremities by making a single incision and using a single disposable device that contains the tools needed for a procedure would decrease the risk of infection, as well as postoperative pain and healing time versus present methods.

The present application fulfills a need in the art for a compact device for uniportal surgery in the lower extremities that eliminates the need for a separate device, such as an obturator, for filling the cannula during insertion and eliminates the need to remove the endoscope in order to insert a blade or blade assembly.

SUMMARY

One aspect of the present application relates to a uniportal surgical device comprising: (a) a two-part housing, wherein the two-part housing is divided into a revolver housing and a latch housing, the revolver housing being distal to the latch housing; (b) a slotted clear cannula attached to the distal end of the revolver housing, said slotted clear cannula comprising a cannula body having a proximate end and a distal end, and a longitudinal slot extending from said proximate end of said cannula to the proximity of said distal end of said cannula; (c) a revolver assembly located within the revolver housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly for inserting a viewing device having a proximate end and a distal end, wherein the proximate end of the tube assembly attaches to the latch assembly and the distal end of the tube assembly slides through the revolver housing and extends through the revolver, wherein the distal end of the tube assembly is capable of entering the slotted clear cannula from the proximate end of said clear cannula, wherein the latch housing comprises a two-button pinch-type scope lock assembly for holding a viewing device in a stationary position relative to the tube assembly, wherein compressing the buttons releases the viewing device and wherein the latch housing is movable and rotatable relative to the revolver housing.

Another aspect of the present application relates to a uniportal surgical kit. The kit comprises the uniportal surgical device of the present application. In some embodiments, the kit further comprises an endoscope, a scalpel, an elevator and/or a dissector.

Still another aspect of the present application relates to a method for a performing a uniportal surgical procedure on a target tissue. The method comprises the steps of: establishing an entry portal in the subject; inserting into the entry portal the cannula of the uniportal surgical device of the present application; extending the cannula through the entry portal to the target tissue; advancing a viewing device into the cannula to visualize a target tissue; and advancing the blade into the cannula until a desired cut is made on the target tissue.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or housing of the device, or may be at an angle to that level plane, allowing some upward or downward movement of elements moving along the horizontal plane with respect to the level plane.

As used herein, the term "button" refers to a knob or disc that, when pressed, compresses a spring within the device and allows a viewing device to be inserted into, moved within or withdrawn from a channel within the device.

As used herein, the term "plantar fascia release" also refers to "plantar fasciotomy."

One aspect of the present application relates to a compact device for performing endoscopic and arthroscopic surgical procedures. In some embodiments, the surgical procedure is a uniportal surgical procedure. The device comprises a slotted clear cannula that is attached to a housing. The housing has a generally flattened shape. In some embodiments, the housing has an oval or elliptical shape in cross-section. This facilitates the holding of the housing, for example when used in procedures performed on the lower extremities of the body. The cannula comprises an open longitudinal slot that extends from the proximal end to the proximity of the distal end of the cannula.

The device housing is generally divided into two subsections: a distal subsection and a proximal subsection. The distal subsection (revolver housing) of the housing attaches at its distal end to the proximal end of the cannula and comprises storage of tools, such as a blade and a scraper, and a manual selector for choosing one of said tools to be attached to a scope and advanced into said cannula. In addition, the distal end of the housing comprises indents on the lateral sides to facilitate grasping and a secure hold by a practitioner.

The proximal subsection (latch housing) of the housing comprises a lock mechanism for securing a viewing device, such as an endoscope or arthroscope into the device. The viewing device is fed into the proximal end of the proximal subsection of the housing, extends through the locking mechanism and into a tube that is secured to the distal end of the proximal subsection of the housing. The tube extends into the distal subsection of the housing, connecting the proximal subsection of the housing to the distal subsection of the housing, as well as through it into the cannula.

Near the distal end of the tube is a tube locator, which provides an attachment point to the tube for tools stored within the housing. A tool for attachment to the tube locator is selected by moving the manual selector to the correct position. The viewing device slides into the tube from the proximal end to the distal end, protruding from the distal end so that tissues and the action of the tool attached to the tube locator can be observed.

In some embodiments, the clear cannula of the device has a closed distal end, allowing the cannula to be inserted through a portal (such as an incision) without the use of a cannula filling instrument, such as an obturator. The clear cannula allows the practitioner a 360 degree field of vision around the cannula through the use of a viewing device, such as an endoscope or arthroscope, inserted into the central lumen of the cannula. This allows the practitioner to visualize all of the tissues surrounding the cannula from the point of initial insertion to and beyond the tissue targeted for a desired surgical procedure. In some embodiments, the clear cannula comprise a blunt leading edge that is designed to serve as an obturator. The blunt leading edge allows the cannula to be inserted through an entry point and advanced to and/or beyond the target tissue without the need to first insert an instrument, such as an elevator, through the incision to first separate tissues and make a path for the cannula. An advantage of this design is that it eliminates a step in the surgical procedure. Another advantage is that it eliminates a step requiring a blind insertion of an instrument into a patient, as the insertion and advancement path of an elevator cannot be easily visualized by the practitioner. In some embodiments, the clear cannula with a sharpened leading edge allows the practitioner to insert viewing device into the clear cannula and visually monitor the insertion of the cannula and creation of a channel from the point of initial insertion to, or beyond, the target tissue. This allows the practitioner to penetrate into the tissue only as far as is necessary for performing the desired procedure, as well as avoiding tissues or structures that could be damaged, such as nerves or blood vessels, by blind insertion of a separating tool, such as an elevator.

The use of the present device is exemplified in this application for, but not limited to, surgical division of fascia, ligaments or tendons in a lower extremity. Some other non-limiting uses for the present device include, for example, other divisions or partial separation of a tendon or ligament, cutting, dividing, separating or making an incision in connective tissue, muscle, cartilage, membranes, skin, other body tissues or organs or any other use of the device that can be envisioned or carried out by the practitioner. As used herein, the term "practitioner" refers to one of skill in the art or any other user of the present device.

Surgical procedures that can be performed with a cannula or device of the present application include, but are not limited to plantar fascia release, lateral release for patella realignment, release of the posterior and other compartments of the leg, release of fascial compartments in the lower extremities, relieving the compression of a nerve by a ligament pulley or tunnel, and releasing the travel of a ligament or tendon through a pulley or tunnel. In some embodiments, the cannula or device of the present application is used for harvesting blood vessel, including vein or artery. In some embodiments, the cannula or device of the present application is used for harvesting the greater saphenous vein, in conjunction with a coronary bypass procedure or for a reconstructive surgical procedure. Due to the self-contained nature of the device, the present device is particularly well suited for, but not limited to, uniportal endoscopic or arthroscopic surgical procedures.

A particular aspect of the present application relates to a surgical device. The surgical device comprises (a) a device housing, wherein the device housing is divided into a revolver housing and a latch housing, the revolver housing being distal to the latch housing; (b) a slotted clear cannula attached to the distal end of the revolver housing, said slotted clear cannula comprising a cannula body having a proximate end and a distal end, and a longitudinal slot extending from said proximate end of said cannula to the proximity of said distal end of said cannula; (c) a revolver assembly located within the revolver housing, comprising: a slide lock having a proximate end, a distal end and a first notch at said distal end; a blade assembly; and a circular revolver body comprising a selector switch; wherein said blade assembly resides at said first notch of said slide lock in a pre-deployment position and wherein said selector switch allows selection of said blade for deployment; and (d) a tube assembly for inserting a viewing device having a proximate end and a distal end, wherein the proximate end of the tube assembly attaches to the latch assembly and the distal end of the tube assembly slides through the revolver housing and extends through the revolver, wherein the distal end of the tube assembly is capable of entering the slotted clear cannula from the proximate end of said clear cannula; wherein the latch housing comprises a scope lock assembly for holding a viewing device in a stationary position relative to the tube assembly, wherein the latch housing is movable and rotatable relative to the revolver housing.

In some embodiments, the slide lock further comprises a second notch at said distal end and said revolver assembly further comprises a scraper; wherein said scraper resides at said second notch of said slide lock in a pre-deployment position and wherein said selector switch allows selection of said scraper or said blade for deployment.

In other embodiments, the scope lock assembly is a two-button pinch-type assembly, wherein compressing the buttons releases the viewing device and allows movement of the viewing device through the tube assembly.

In still other embodiments, the distal end of the latch housing assembly is lockable to the proximate end of the revolver housing.

In some embodiments, the default condition of the scope lock assembly is immobilization of the viewing device relative to the tube assembly.

In other embodiments, the distal end of the slotted clear cannula is a closed end that is shaped to serve as an elevator. In some further embodiments, the distal end of the slotted clear cannula forms an angle with the cannula body, wherein said angle is in the range of 165-145 degrees.

Another aspect of the present application relates to a surgical kit comprising a surgical device and a scalpel. The surgical device comprises (a) a device housing, wherein the device housing is divided into a revolver housing and a latch housing, the revolver housing being distal to the latch housing; (b) a slotted clear cannula attached to the distal end of the revolver housing, said slotted clear cannula comprising a cannula body having a proximate end and a distal end, and a longitudinal slot extending from said proximate end of said cannula to the proximity of said distal end of said cannula; (c) a revolver assembly located within the revolver housing, comprising: a slide lock having a proximate end, a distal end and a first notch at said distal end; a blade assembly; and a circular revolver body comprising a selector switch; wherein said blade assembly resides at said first notch of said slide lock in a pre-deployment position and wherein said selector switch allows selection of said blade for deployment; and (d) a tube assembly for inserting a viewing device having a proximate end and a distal end, wherein the proximate end of the tube assembly attaches to the latch assembly and the distal end of the tube assembly slides through the revolver housing and extends through the revolver, wherein the distal end of the tube assembly is capable of entering the slotted clear cannula from the proximate end of said clear cannula; wherein the latch housing comprises a scope lock assembly for holding a viewing device in a stationary position relative to the tube assembly, wherein the latch housing is movable and rotatable relative to the revolver housing.

In some embodiments, the surgical kit further comprises an viewing device. In some further embodiments, the viewing device is an endoscope. In other further embodiments, the viewing device is an arthroscope.

Still another aspect of the present application relates to a method for a performing a surgical procedure on a target tissue using a surgical device comprises (a) a device housing, wherein the device housing is divided into a revolver housing and a latch housing, the revolver housing being distal to the latch housing; (b) a slotted clear cannula attached to the distal end of the revolver housing, said slotted clear cannula comprising a cannula body having a proximate end and a distal end, and a longitudinal slot extending from said proximate end of said cannula to the proximity of said distal end of said cannula; (c) a revolver assembly located within the revolver housing, comprising: a slide lock having a proximate end, a distal end and a first notch at said distal end; a blade assembly; and a circular revolver body comprising a selector switch; wherein said blade assembly resides at said first notch of said slide lock in a pre-deployment position and wherein said selector switch allows selection of said blade for deployment; and (d) a tube assembly for inserting a viewing device having a proximate end and a distal end, wherein the proximate end of the tube assembly attaches to the latch assembly and the distal end of the tube assembly slides through the revolver housing and extends through the revolver, wherein the distal end of the tube assembly is capable of entering the slotted clear cannula from the proximate end of said clear cannula; wherein the latch housing comprises a scope lock assembly for holding a viewing device in a stationary position relative to the tube assembly, wherein the latch housing is movable and rotatable relative to the revolver housing. The method comprises the steps of establishing an entry portal in said subject; inserting into said entry portal said cannula of said surgical device; extending said cannula through said entry portal to said target tissue; advancing a viewing device into said cannula visualize a target tissue; and advancing said blade into said cannula until a desired cut is made on said target tissue.

In some embodiments, the surgical procedure is a uniportal surgical procedure. In other em
bodiments, the surgical procedure is an endoscopic procedure.

In still other embodiments, the surgical procedure is an arthroscopic procedure.

In particular embodiments establishing an entry portal comprises making an incision.

In some embodiments, the desired cut is division of said target tissue.

In other embodiments, the slide lock of said surgical device further comprises a second notch at said distal end and said revolver assembly further comprises a scraper; wherein said scraper resides at said second notch of said slide lock in a pre-deployment position and wherein said selector switch allows selection of said scraper or said blade for deployment, in some further embodiments, the method further comprises the step of advancing said scraper into said cannula to remove tenosynovium, adipose tissue or ligament sheath.

In still other embodiments, the surgical procedure is selected from the group consisting of fascia release, lateral release for patella realignment, release of the extensor tendons, release of the posterior or other compartments of the leg, and blood vessel harvesting. In some further embodiments, the fascia release is selected from the group consisting of forearm fasciotomy, plantar fasciotomy, fasciotomy for compartment syndrome, and leg fasciotomy. In other further embodiments, the blood vessel is a vein or artery.

Figure 1:
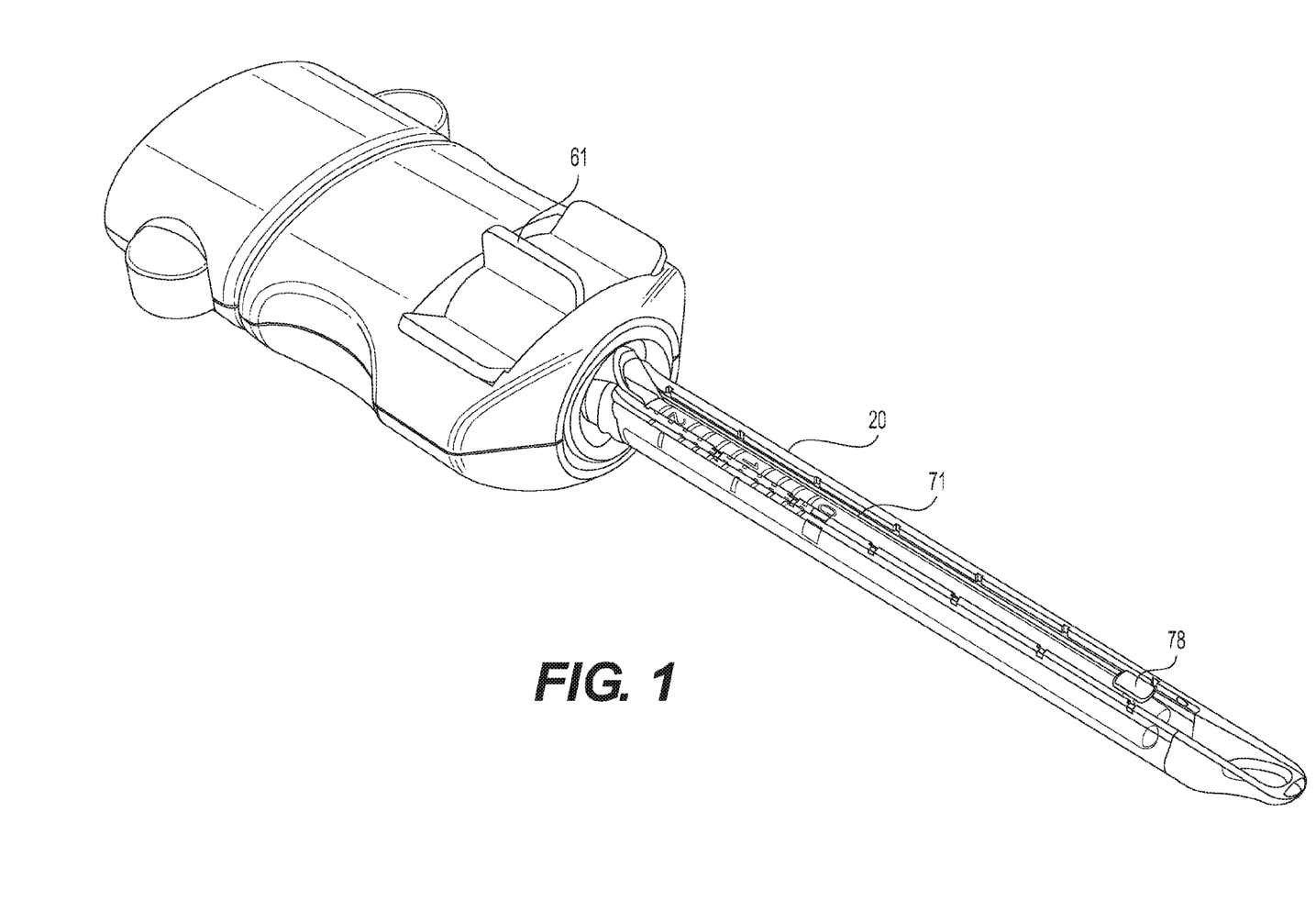
FIG. 1 is a perspective view of an embodiment of the device of the present application.

FIG. 1 shows an embodiment of the present application wherein the device 100 comprises a clear cannula 20 and a two-part housing 10 and a clear cannula 20. The two-part housing 20 contains a revolver housing 30 that houses a rotational switch 61 for selecting the tool to advance into the cannula 20, and a latch housing 130 that houses a scope lock assembly with two shaft lock buttons 150 and 151. The body of the housing is generally oval in cross-section with the flattened design of the housing being advantageous for surgical procedures in the lower extremities.

Figure 2:
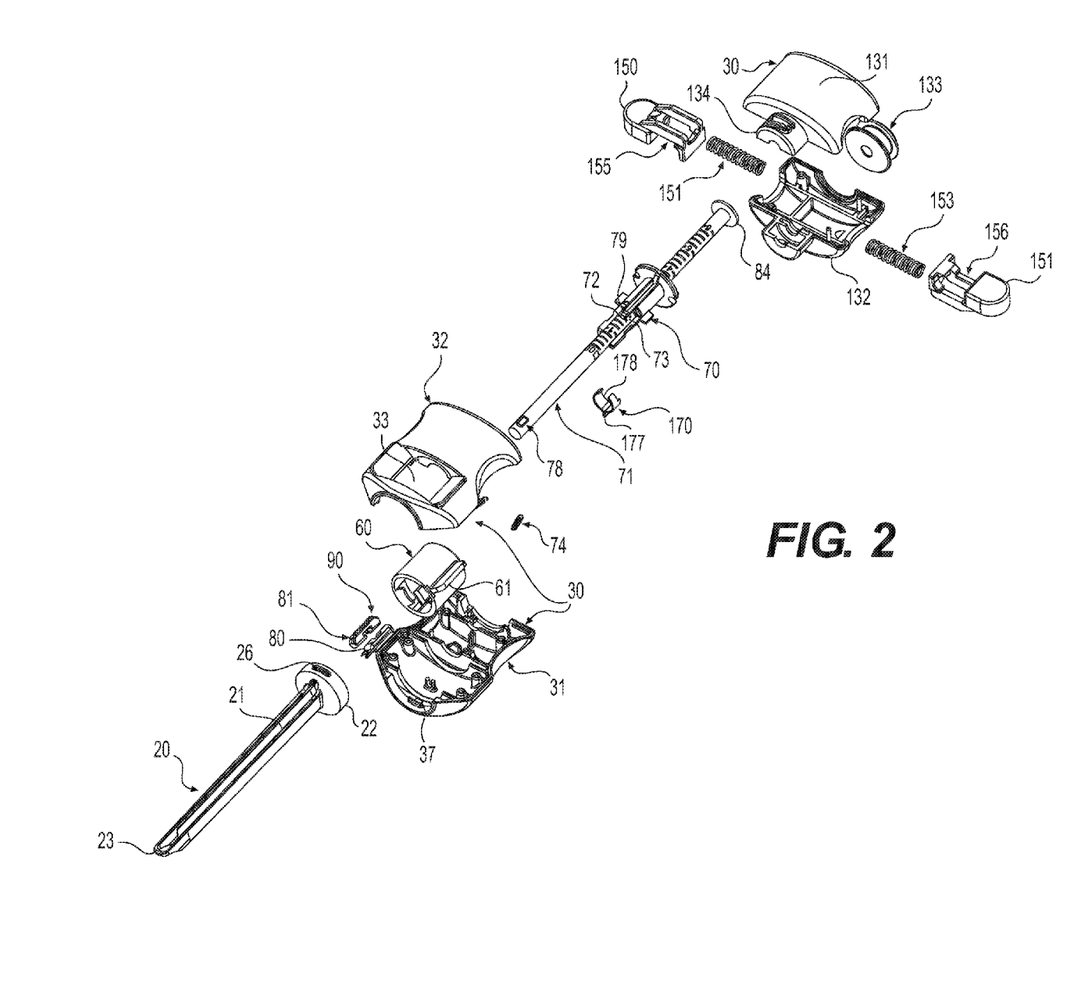
FIG. 2 is an exploded view of the embodiment of the embodiment depicted in FIG. 1.

FIG. 2 depicts an exploded view of the present device of FIG. 1. The revolver housing 30 is generally oval in cross-section and is comprised of a bottom half 31 and a top half 32. The top half 32 comprises an opening 33 that the switch 61 of the revolver 60 protrudes through.

The revolver 60 encircles a slide lock 70 (or inner sleeve 70) that encircles a guidance tube or tube assembly 71. The slide lock 70 comprises notches 72, 73 and tab 79 separating the notches 72, 73 which provide pre-deployment resting places for a blade 80 (mounted on a blade sled 81) and a scraper 90 in the revolver housing 30. The blade sled 81 and the scraper 90 are retained in their notches 72,73 while in their pre-deployment positions by a rotary clip 170. The slide lock 70 works in concert with the revolver 60 in order to bring the blade 80 or scraper 90 into the proper orientation for deployment into the slot 21 of the cannula 20. The tube assembly 71 provides a path for deploying an endoscope through the device and into the cannula 20. The tube assembly 71 also provides, at its distal end, a mounting point or tube locator 78 that the blade sled 81 or scraper 90 is rotated onto for deployment. The tube assembly 71 is advanced along the deployed endoscope into the cannula 20, thereby deploying the blade 80 or scraper 90 into the slot 21 of the cannula 20. An extension spring 74 extending from the slide lock 70 to a tab on the inside of the lower half 32 of the revolver housing 30 provides tension so that the slide lock 70 and revolver 60 remain in the selected position.

Turning briefly back to the view of the device depicted in FIG. 1, wherein the tube assembly 71 can be seen extended into the cannula 20. The selector switch 61 is set for "SCOPE" and neither the blade tool nor the scraper is attached to the tool selector 78.

Returning to the exploded view of the embodiment of the device in FIG. 2, one particular feature of this embodiment is the scope lock assembly within the latch housing 130, also comprising an upper half 131 and lower half 132, which can also serve as a handle for advancing or withdrawing the tube assembly 71 into/from the slotted clear cannula 20 of the device. In such an embodiment, the tube stop 84 element of the tube assembly 71 is retained within the neck 134 of the scope lock assembly 130. The tube stop 84 can freely rotate within the neck 134 so that the latch housing 130 can be twisted to lock into the back of the revolver housing 30. The proximal opening of the scope lock assembly 130 is sealed with a shaft inlet 133. In some embodiments, the scope lock assembly comprises a four part locking mechanism comprising two shaft lock buttons 150,151 and a pair of shaft lock springs 152,153. The shaft lock buttons 150,151 each comprise a shaft channel 155,156 that extends past a viewing device, such as an endoscope or arthroscope, that is passed through the latch housing 130 into the tube assembly 71. When the shaft lock buttons 150,151 are depressed, the shaft lock springs 152, 153 are compressed and the viewing device can slide freely through the shaft channels 155,156 and can slide into or out of the tube assembly 71. When the shaft lock buttons 150,151 are released, the shaft lock springs 152,153 push the opposite sides of the shaft channels 155,156 against the viewing device, locking the position of viewing device relative to the tube assembly 71. When the viewing device is locked into the shaft channels 155,156, the latch housing 130 serves as a handle to move the viewing device and tube assembly 71 forward and backward through the revolver housing 30 into and out of the cannula 20. The latch housing 130 can also be rotated, allowing the viewing of surrounding tissues through the clear material of the cannula 20. This embodiment of a scope lock mechanism is an exemplary embodiment and is not limiting on the device. Any scope lock device that can be envisioned to function with the present device is within the scope of the present application.

Referring again to FIG. 2, the clear cannula 20 of the device comprises a slot 21 extending longitudinally from the proximity of the proximal end 22 to the proximity of the distal end 23. Also visible are the depressions, slots, or holes 26 that engage with tabs or pins on the front of the housing. In some embodiments, the sides of the slot 21 comprise texture or tick marks that are at a measured distance from one another down the length of the slot 21. In some embodiments, the distal end 23 of the cannula 20 is a blunted and closed to eliminate the need of an obturator. Since the cannula 20 is made from a transparent material, the closed distal end 23 would still allow observation of the surrounding tissue with an endoscope. In some embodiments, the closed distal end 23 is turned up and has a sharpened edge that allows the cannula to separate tissues without the need to first use an elevator. In some embodiments, the distal end 23 is a tapered, tongue-shaped protrusion that forms an angle with the body of the cannula 20 that may serve as an elevator. In some embodiments, the cannula 20 has a total length in the range of 25-200 mm, 25-150 mm, 25-100 mm, 25-75 mm, 25-50 mm, 50-200 mm, 50-150 mm, 50-100 mm, 50-75 mm, 75-200 mm, 75-150 mm, 75-100 mm, 100-200 mm, 100-150 mm or 150-200 mm. In other embodiment, the cannula 20 has a total length of about 50 mm, about 60 mm, about 70 mm, about 75 mm, about 80 mm, about 90 mm or about 100 mm. In one embodiment, the cannula 20 has a total length of about 76.2 mm. In another embodiment, the cannula 20 has a total length of about 71 mm.

Referring again to FIG. 2, in some embodiments, the top half 32 and bottom half 31 of the revolver housing 30 may comprise, inside their distal ends, a tab or pin 37 that engages with the depression, slot, or hole 26 located on the proximate end of the cannula 20. In some embodiments, rather than individual or multiple tabs or pins at the distal end of the housing, the tab or pin 37 may be an annular ring that runs around the inside of the distal end of the housing 30 and engages an impression or groove that runs all the way around the outside of the proximate end of the cannula.

In some embodiments, the rotary clip 170 comprises a tab 177 that engages with the inside of the revolver housing 30 to prevent the rotary clip 170 from rotating or sliding. The top of the rotary clip 170 is open 178, so that when the scraper 90 or blade sled 81 is rotated into the deployment position, it can be deployed through the rotary clip 170 and into the cannula 20. The rotary clip may be manufactured from any suitable material, such as plastic, stainless steel, aluminum, or metal alloys. In some embodiments, the rotary clip 170 may be formed, cut, stamped, cast or milled as a flat piece, from a malleable metal such as SS 303 and then formed into the final shape of being an open-topped ring with a tab at the bottom. In other embodiments, the rotary clip 170 may be formed, cut, molded, 3D-printed, cast or milled from a suitable material as an open-topped ring with a tab at the bottom.

Regarding the blade 80 and blade sled 81 (also known as the blade assembly), the bade sled 81 provides a stable platform for the blade 80 that fits within the confines of the slot 21 of the cannula 20 and prevents lateral movement of the blade 80 during deployment. The blade sled 81 comprises a notch that positively engages with the tool selector 78 of the tube assembly 71. When the selector switch 61 of the revolver 60 is rotated to the "BLADE" position, the blade assembly is rotated upward by the slide lock 70 so that the notch in the blade sled 81 of the blade assembly slides onto and engages the tool selector 78. The tool selector 78 then firmly holds the blade assembly 190 on the surface of the tube assembly 71. Advancing the tube assembly 71 also advances the blade assembly into the cannula 20. The blade assembly protrudes through the longitudinal slot 21 in the cannula 20 and advancement of the blade assembly with the tube assembly 71 moves the blade 80 into contact with the target tissue. Further advancement of the blade assembly allows the blade 80 to separate the target tissue. In some embodiments, the end of the blade sled 81 opposite the cutting surface of the blade 80 is angled so that it does not catch tissues as it is being withdrawn through the slot 21 of the cannula 20. The width of the blade sled 81 is such that it securely contacts the side walls of the slot 21 in the cannula 20 but is still able to be advanced or withdrawn through the slot without an amount of friction that would impede its progress. The sides of the blade 80 do not contact the walls of the slot 21. In particular embodiments, the bottom surface of the blade sled 81 is curved to match the curvature of the tube assembly 71, thus inhibiting or preventing side to side motion, or wobble, of the blade assembly during deployment. In some embodiments, the blade 80 comprises a tab that embeds into the blade sled 81. In some embodiments, the blade 80 is secured into the blade sled 81 using a pin or screw. In such an embodiment, the blade 80 may be replaceable in the blade assembly, allowing the use of blades with different profiles particularly suited for a specific surgical procedure. For example, it may be desirable to use a hook blade in some situations, where the cutting surface faces back towards the revolver housing 30 of the device, allowing the practitioner to move the blade past the target tissue and separate the target tissue by pulling the blade backwards, rather than separating the target tissue upon advancing the blade. The blade sled 81 of the blade assembly can be formed of any medically acceptable material, such as a plastic or ceramic, as it may come in contact with body tissues. In a particular embodiment, the blade sled 81 is formed of polycarbonate. In some embodiments, the blade assembly may be replaced in the device with any other suitable blade tool that engages with the tool selector.

In particular embodiments, the blade 80 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODIFIED 440-A stainless steel. The blade is optionally flash electropolished or passivated per ASTM A967, or by any other method that delivers a similar finish. The cutting edges are machine finished and must be sharp. In a particular embodiment, the steel of the blade is heat-treated to Rockwell C hardness of about 50-72. In a more particular embodiment, the steel of the blade is heat-treated to R30N 75.7-77.5 (Rockwell C hardness of 58-60).

Similar to the blade sled 81, the base of the scraper 90 comprises a notch that positively engages with the tool selector 78 of the tube assembly. When the selector switch 61 of the revolver 60 is rotated to the "SCRAPER" position, the scraper 90 is rotated upward by the slide lock 70 so that the notch in the base of the scraper 90 slides onto and engages the tool selector 78. The tool selector 78 then firmly holds the scraper 90 on the surface of the tube assembly 71. Advancing the tube assembly 71 also advances the scraper 90 into the cannula 20. The teeth of the scraper 90 protrude through the longitudinal slot 21 in the cannula 20 and advancement of the scraper 90 with the tube assembly 71 moves the teeth into contact with the target tissue. Further advancement of the blade assembly allows the teeth to rake across the target tissue. In particular embodiments, the distal end and proximate end of the base are rounded and angled downwards so that they do not catch tissues as the scraper 90 is being advanced or withdrawn through the slot 21 of the cannula 20. The width of the base is such that it securely contacts the side walls of the slot 21 in the cannula 20 but is still able to be advanced or withdrawn through the slot without an amount of friction that would impede its progress. In particular embodiments, the bottom surface of the base is curved to match the curvature of the tube assembly, thus inhibiting or preventing side to side motion, or wobble, of the scraper 90 during deployment. The scraper 90 can be formed of any medically acceptable material, such as a plastic, ceramic, stainless steel, or nitinol, as it does come in contact with body tissues. In a particular embodiment, scraper 90 is formed of polycarbonate.

In regard to the tube assembly 71, in some embodiments, the tube assembly 71 is composed of stainless steel, preferably AISI 304 stainless steel. However, the tube assembly can be made from any suitable material including, but not limited to, aluminum, titanium, nitinol or other metal alloys, or plastic. In some embodiments where the tube assembly 71 is made of plastic, the plastic may be clear, allowing visualization with an viewing device of tissues surrounding the cannula 20 through the body of the tube assembly 71.

The tube assembly 71 comprises near its distal end a tool selector 78. The tool selector 78 is directly on top of the tube assembly 71. When the selector switch 61 of the revolver 60 is positioned at the "SCOPE" setting, no tools are engaged with the tool selector 78 and the tube assembly 71 can be advanced into the cannula 20 without the blade assembly or scraper 90. When the selector switch 61 of the revolver 60 is moved to the "BLADE" setting, the revolver 60 rotates the slide lock 70 such that the notch 72 holding the blade sled 81 is moved to the top of the tube assembly 71 and the notch in the bottom surface of the blade sled 81 is positively engaged with the tool selector 78. Advancement of the tube assembly 71 would cause the advancement of the blade assembly into and down the length of the cannula 20, protruding through the slot 21. When the selector switch 61 of the revolver 60 is mover to the "SCRAPER" setting, the revolver 60 rotates the slide lock 70 such that the notch 73 holding the scraper 90 is moved to the top of the tube assembly 71 and the notch in the bottom surface of the scraper 90 is positively engaged with the tool selector 78. Advancement of the tube assembly 71 would cause the advancement of the scraper 90 into and down the length of the cannula 20, protruding through the slot 21. In some embodiments, the tool selector 78 is welded, preferably laser welded, onto the top of the tube element of the tube assembly 71. In a preferred embodiment, the tool selector 78 is welded all around at its base to the tube element. In particular embodiments, the strength of the weld should be able to withstand the application of 5 in-lbs. torque to the unit, more particularly 10 in-lbs. torque. The tube assembly 71 further comprises a tube stop 84 at the proximate end of the tube element. The tube stop 84 retains the proximal end of the tube assembly 71 in the scope lock housing 130 of the device, preventing the tube assembly from passing forward completely through the proximate end of the scope lock housing 130. In some embodiments, the tube stop 84 is welded flush with the proximal end of the tube element of the tube assembly. In particular embodiments, the weld should be strong enough to withstand at least 10 lbs. normal force to the face, more particularly 20 lbs. normal force to the face.

Figure 3:
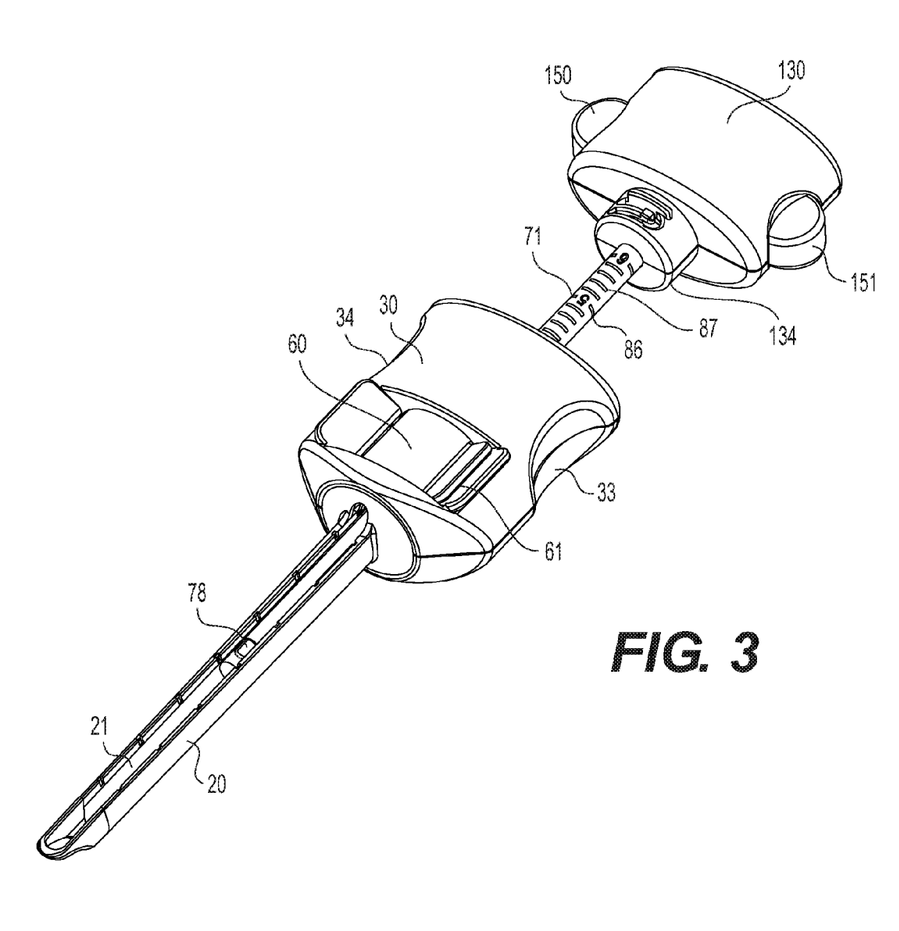
FIG. 3 shows an additional perspective view of the embodiment depicted in FIG.

The tube assembly 71 can optionally be marked on the top or side surface with gradations 86,87 as exemplified in FIGS. 2 and 3 to show the distance that the tube assembly 71 has been advanced into the cannula 20. As a non-limiting example, major gradations 86 can be made to show each centimeter in distance that the tube assembly 71 has been advanced into the cannula 20, with minor gradations 87 between them to show, for example, each 1, 2, 2.5 or 5 millimeters. While the gradations can be applied to the tube assembly 71 by any means known in the art, it is preferable to lasermark the gradations on the tube assembly 71 for accuracy and permanence. In some embodiments, the distance between the major or minor gradations 86,87 corresponds to the distance between the tick marks 27 in the sides of the slot 21 in the cannula 20. In some embodiments, the tick marks minimally engage with the tool selector 78 carrying the blade and/or scraper as it advances, or retreats, along the length of the slot 21 to allow the practitioner to feel, or otherwise determine, how far the tube assembly 71 has advanced along the slot.

In some embodiments, the tube stop 84 of the tube assembly 71 is trapped within the neck 134 of the scope lock assembly, allowing the latch housing 130 to be used as a handle for advancing/withdrawing the tube assembly 71 through the revolver housing 30 of the device and into/from the clear cannula 20. The tube stop 84 can rotate within the neck 134 of the latch housing 130 so that, in some embodiments, the latch housing 130 can be twisted to lock/unlock it to/from the revolver housing 30, for example to keep the scope in a locked position within the clear cannula 20 during insertion or withdrawal of the cannula through a body opening or a channel between/through a body tissue during an endoscopic surgical procedure.

Kit

Another aspect of the present application relates to an instrument kit for implementing an endoscopic surgical procedure. The kit comprises the endoscopic surgical blade assembly of the present application. In some embodiments, the instrument kit contains an endoscopic surgical device comprising a slotted clear cannula, a blade and a housing, wherein the cannula is attached to the housing, and further wherein the blade is enclosed in the housing and is slidable into the cannula.

In some embodiments, the endoscopic surgical device comprises a slotted clear cannula, a scraper, a blade and a housing, wherein the cannula is attached to the housing. In a pre-deployment configuration, the scraper and the blade are enclosed in the housing, the blade and scraper are individually selectable for deployment orientation, and the blade or scraper is slidable into the cannula in a deployment orientation.

In some embodiments, the instrument kit comprises components and implements useful for endoscopic procedures.

In one embodiment, the instrument kit further includes an endoscope sized for insertion into the slotted clear cannula for direct visualization of an operative site.

In another embodiment, the instrument kit further includes a scalpel.

In another embodiment, the instrument kit further includes an elevator.

In another embodiment, the instrument kit further comprises at least one of scissors, a clamp, hemostat or retractor.

In another embodiment, the instrument kit further comprises a needle and suture material.

In another embodiment, the instrument kit further includes a depth gauge mountable to a leading end of the endoscope.

In another embodiment, the instrument kit further includes a stop device mountable on or in the cannula to prevent excessive penetration at a surgical site by the cutting instrument.

In another embodiment, the instrument kit further includes a curved dissector.

Method for Endoscopic or Arthroscopic Surgery

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures including, but not limited to, plantar fascia release, lateral release for patella realignment, release of the posterior and other compartments of the leg, release of fascial compartments in the lower extremities, relieving the compression of a nerve by a ligament pulley or tunnel, and releasing the travel of a ligament or tendon through a pulley or tunnel. The cannula or device of the present application can be used for blood vessel harvesting, including vein or artery, for example to provide blood vessel graft material, for example from the greater saphenous vein, in conjunction with a coronary bypass procedure or for a reconstructive surgical procedure.

One embodiment of the present application relates to a method for a performing a uniportal endoscopic surgical procedure a target tissue in a subject. Generally, the endoscopic surgical procedure requires the establishment of an entry portal. In some embodiments of the present application, the entry portal is established to the proximate side of the target tissue. In other embodiments of the present application, the entry portal is established to the distal side of the target tissue.

In some embodiments, the establishing an entry portal comprises making an incision.

In some embodiments, following the establishment of an entry portal, a blunt instrument, such as an elevator, is inserted through the portal to establish an opening in the underlying tissue between the portal and the target tissue. In other embodiments, following the establishment of an entry portal, an opening in the underlying tissue between the portal and the target tissue is established by inserting a clear slotted cannula having a sharpened front edge for separating tissues. In a further embodiment, a viewing device, such as an endoscope, is inserted into the clear slotted cannula in order to visualize the procedure of establishing an opening in the underlying tissue between the portal and the target tissue.

In one embodiment, an endoscopic surgical device comprising a slotted clear cannula, a blade and a housing, wherein the cannula is attached to the housing, and further wherein the blade is enclosed in the housing and is slidable into the cannula, is inserted into the entry portal and extended through to the target tissue.

In some embodiments, the endoscopic surgical device comprises a slotted clear cannula, a scraper, a blade and a housing, wherein, the cannula is attached to the housing, in a pre-deployment configuration the scraper and the blade are enclosed in the housing, the blade and scraper are individually selectable for deployment orientation, and in deployment orientation the blade or scraper are slidable into the cannula. In some further embodiments, the device comprises a tube assembly that allows a viewing device to be inserted through a central lumen, wherein the tube assembly engages separately with the blade or the scraper and advancing the tube assembly into the slotted clear cannula advances the selected blade or scraper.

In some embodiments, the endoscopic surgical device further comprises a mechanism for locking the viewing device in a fixed position relative to the tube assembly. In some further embodiments, the scope lock assembly engages with the tube assembly and is used as a handle for advancing or withdrawing the tube assembly into or from the slotted clear cannula.

An endoscope is inserted through the housing and into the cannula to view the target tissue and the surrounding tissues, assuring that the slot of the cannula is in proper orientation to the target tissue.

In one particular embodiment, the operative procedure is plantar fascia release.

In another particular embodiment, the operative procedure is lateral release for patella realignment.

The present invention is further illustrated by the following examples which should not be construed as limiting. The contents of all references, patents and published patent applications cited throughout this application, as well as the Figures, are incorporated herein by reference.

Example 1: Uniportal Endoscopic Plantar Fascia Release

In a patient presenting with plantar fasciitis, an incision is made on the medial side of the foot, ahead of the tubercule of the calcaneus.

An endoscopic viewing device is inserted into an endoscopic surgical device having a slotted clear cannula that comprises a sharpened front edge for separating tissues. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The slotted clear cannula having a sharpened front edge is introduced into the incision and used to create a plane under the plantar fascia, with the slot of the cannula facing the plantar fascia. The procedure is observed with the viewing device.

Following the creation of the plane, the tube assembly, still with the viewing device locked in place in relation to the tube assembly, is withdrawn back into the housing of the device. In the event that adipose tissue obscures visualization of the plantar fascia, the revolver of the device is turned to select deployment orientation of the scraper. The tube assembly is advanced into the cannula and the scraper protrudes through the slot of the cannula. The adipose tissue is removed with the scraper and the tube assembly is retracted, bringing the scraper back into the housing of the device. The revolver of the device is rotated to restore the scraper back to its pre-deployment configuration in the device.

The plantar fascia is again visualized with the endoscope, the tube assembly is retracted and the revolver of the device is turned to select deployment orientation of the blade. The tube assembly is advanced with the endoscope into the cannula and the blade protrudes through the slot of the cannula. The blade is advanced into contact with the plantar fascia. The blade is further pushed forward, dividing the plantar fascia. If the fascia is not completely divided by the first pass of the blade, additional passes may be performed. The tube assembly is retracted, bringing the blade back into the housing of the device. The revolver of the device is rotated to restore the blade back to its pre-deployment configuration in the device.

The cut edges of the plantar fascia and the overlying muscle tissue is visualized through the endoscope.

While visualizing the overlying muscle tissue, release may be confirmed by passive manipulation of the ball of the foot.

The cannula is removed from the incision.

The wound is closed and a soft bandage is applied. In some cases, a splint is also applied to immobilize the wrist up to a week.

Example 2: Uniportal Arthroscopic Patellar Release

In a patient presenting with lateral patellar tracking disorder, partial division of the lateral retinaculum is indicated to allow the kneecap to shift into the proper position. The lateral retinaculum runs diagonally downward from the patella toward the lateral side of the leg.

An incision is made to the lateral side of the lower margin of the patella.

An arthroscopic viewing device is inserted into an surgical device having a slotted clear cannula. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The cannula is introduced into the incision and inserted behind the lateral retinaculum, with the slot of the cannula facing the lateral retinaculum. The procedure is observed with the viewing device.

The flexor tendon sheath and the surrounding tissues are again visualized with the arthroscope. A blade is advanced into the cannula and protrudes through the slot of the cannula. The blade is advanced into contact with the lateral retinaculum. The blade is further pushed forward, beginning division of the lateral retinaculum. In some instances, complete division of the lateral retinaculum is not required to allow the patella to shift into the proper position. The blade is retracted.

The cut edges of the lateral retinaculum are visualized through the arthroscope.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A surgical device, comprising:
   (a) a device housing, wherein the device housing is divided into a revolver housing and a latch housing, the revolver housing being distal to the latch housing;
   (b) a slotted clear cannula attached to the distal end of the revolver housing, said slotted clear cannula comprising a cannula body having a proximate end and a distal end, and a longitudinal slot extending from said proximate end of said cannula to the proximity of said distal end of said cannula;
   (c) a revolver assembly located within the revolver housing, comprising:
      a slide lock having a proximate end, a distal end and a first notch at said distal end;
      a blade assembly; and
      a circular revolver body comprising a selector switch;
      wherein said blade assembly resides at said first notch of said slide lock in a pre-deployment position and wherein said selector switch allows selection of said blade for deployment; and
   (d) a tube assembly for inserting a viewing device having a proximate end and a distal end, wherein the proximate end of the tube assembly attaches to the latch assembly and the distal end of the tube assembly slides through the revolver housing and extends through the revolver, wherein the distal end of the tube assembly is capable of entering the slotted clear cannula from the proximate end of said clear cannula;
   wherein the latch housing comprises a scope lock assembly for holding a viewing device in a stationary position relative to the tube assembly, wherein the latch housing is movable and rotatable relative to the revolver housing, wherein said scope lock assembly is a two button pinch-type assembly, wherein compressing the buttons releases the viewing device and allows movement of the viewing device through the tube assembly, and wherein the two buttons are located on opposing sides of the device.

2. The surgical device of claim 1, wherein said slide lock further comprises a second notch at said distal end and said revolver assembly further comprises a scraper; wherein said scraper resides at said second notch of said slide lock in a pre-deployment position and wherein said selector switch allows selection of said scraper or said blade for deployment.

3. The surgical device of claim 1, wherein the distal end of the latch housing assembly is lockable to the proximate end of the revolver housing.

4. The surgical device of claim 1, wherein the default condition of the scope lock assembly is immobilization of the viewing device relative to the tube assembly.

5. The surgical device of claim 1, wherein the distal end of the slotted clear cannula is a closed end that is shaped to serve as an elevator.

6. The surgical device of claim 5, wherein the distal end of the slotted clear cannula forms an angle with the cannula body, wherein said angle is in the range of 165-145 degrees.

7. An surgical kit, comprising the endoscopic surgical device of claim 1 and a scalpel.

8. The surgical kit of claim 7, further comprising an viewing device.

9. The surgical kit of claim 8, wherein the viewing device is an endoscope.

10. The surgical kit of claim 8, wherein the viewing device is an arthroscope.

11. A method for a performing a surgical procedure on a target tissue using the surgical device of claim 1, comprising:
   establishing an entry portal in said subject;
   inserting into said entry portal said cannula of said surgical device;
   extending said cannula through said entry portal to said target tissue;
   advancing a viewing device into said cannula visualize a target tissue; and
   advancing said blade into said cannula until a desired cut is made on said target tissue.

12. The method of claim 11, wherein the surgical procedure is a uniportal surgical procedure.

13. The method of claim 11, wherein the surgical procedure is an endoscopic procedure.

14. The method of claim 11, wherein the surgical procedure is an arthroscopic procedure.

15. The method of claim 11, wherein said establishing an entry portal comprises making an incision.

16. The method of claim 11, wherein said desired cut is division of said target tissue.

17. The method of claim 11, wherein said slide lock of said surgical device further comprises a second notch at said distal end and said revolver assembly further comprises a scraper; wherein said scraper resides at said second notch of said slide lock in a pre-deployment position and wherein said selector switch allows selection of said scraper or said blade for deployment, the method further comprising the step of:

advancing said scraper into said cannula to remove tenosynovium, adipose tissue or ligament sheath.

18. The method of claim 11, wherein the surgical procedure is selected from the group consisting of fascia release, lateral release for patella realignment, release of the extensor tendons, release of the posterior or other compartments of the leg, and blood vessel harvesting.

19. The method of claim 18, wherein the fascia release is selected from the group consisting of forearm fasciotomy, plantar fasciotomy, fasciotomy for compartment syndrome, and leg fasciotomy.

20. The method of claim 18, wherein the blood vessel is a vein or artery.

* * * * *